(12) United States Patent
Zelkha et al.

(10) Patent No.: US 6,797,303 B2
(45) Date of Patent: Sep. 28, 2004

(54) CAROTENOID EXTRACTION PROCESS

(75) Inventors: Morris Zelkha, Omer (IL); Tanya Sedlov, Beer Sheva (IL)

(73) Assignee: Lycored Natural Products Industries Ltd., Beer Sheva (IL)

( * ) Notice: Subject to any disclaimer, the term of this patent is extended or adjusted under 35 U.S.C. 154(b) by 470 days.

(21) Appl. No.: 09/944,105

(22) Filed: Sep. 4, 2001

(65) Prior Publication Data

US 2003/0044499 A1 Mar. 6, 2003

(51) Int. Cl.$^7$ .............................. A23L 1/212; A23L 1/28
(52) U.S. Cl. ..................... 426/431; 426/253; 426/257; 426/616; 426/615
(58) Field of Search ................................ 426/431, 253, 426/616, 257, 615

(56) References Cited

U.S. PATENT DOCUMENTS

| | | | |
|---|---|---|---|
| 5,648,564 A | | 7/1997 | Ausich et al. |
| 5,837,311 A | | 11/1998 | Zelkha et al. |
| 5,871,574 A | * | 2/1999 | Kawaragi et al. |
| 5,876,782 A | | 3/1999 | Sas et al. |
| 6,221,417 B1 | * | 4/2001 | Sas et al. |

* cited by examiner

*Primary Examiner*—Anthony Weier
(74) *Attorney, Agent, or Firm*—Browdy and Neimark, P.L.L.C.

(57) ABSTRACT

Carotenoids are extracted from plant matter by mixing the plant matter and water to obtain a mixture of no greater than 10° Bx, crushing the mixture to obtain a pulp and a serum, and extracting the pulp to obtain a carotenoid containing plant oleoresin.

14 Claims, 2 Drawing Sheets

CAROTENOID EXTRACTION PROCESS

FIELD OF THE INVENTION

Figure 1:
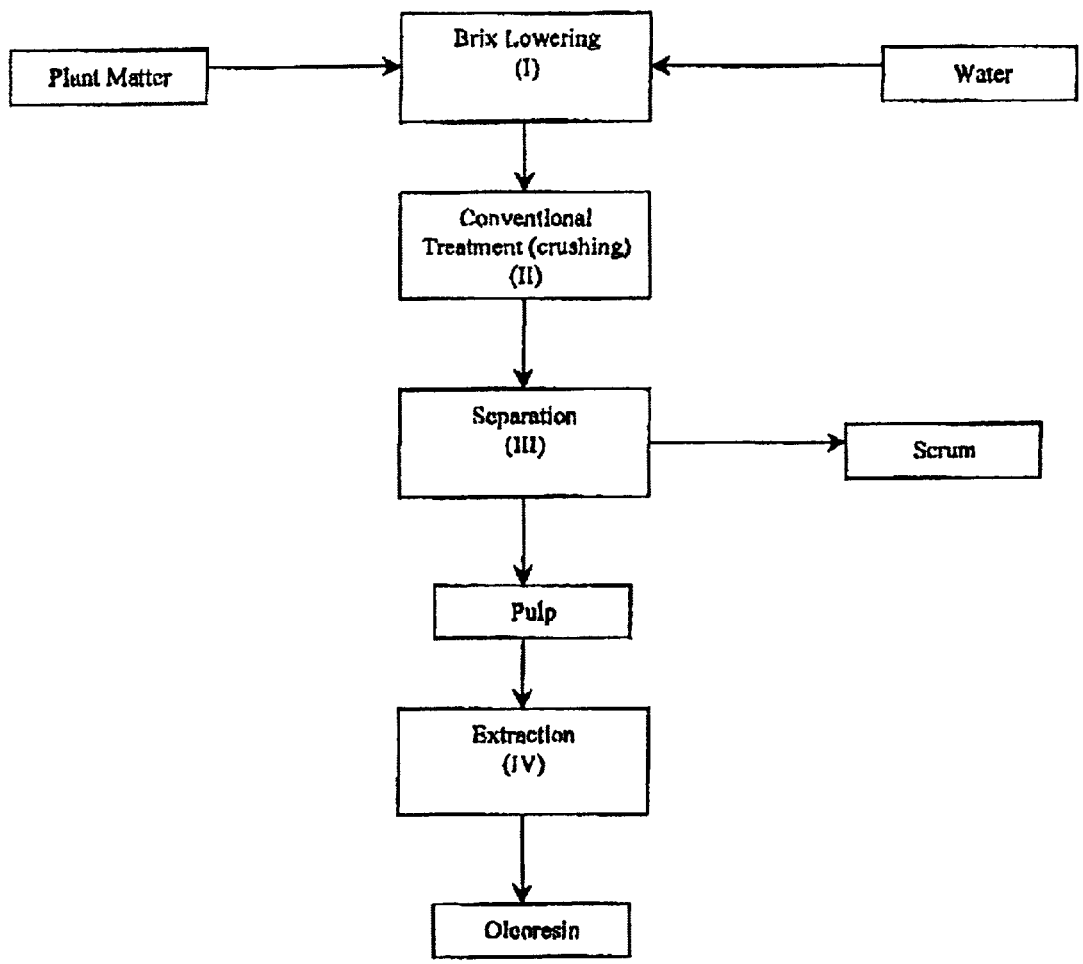

The present invention relates to a process for producing plant oleoresin and extracting carotenoids from plant matter.

BACKGROUND OF THE INVENTION

In recent years the restrictions on the use of solvents in the food industry are rapidly developing. Many organic solvents which were used in the industry to extract lipophilic substances have fallen under regulatory restrictions which forbid or limit the use thereof. Thus, the use of relatively safe solvents such as ethanol and ethyl acetate is rapidly increasing in the industry. However, these solvents are not strongly lipophilic and therefore are not very efficient in extracting lipophilic substances. This problem has been overcome in several extraction processes by technological and engineering solutions. U.S. Pat. No. 5,837,311 incorporated herein by reference, discloses a process for obtaining tomato oleoresin from fresh tomatoes which have Brix of about 5°, wherein suitable extracting solvents are selected according to certain solubility parameters.

Other carotenoid extraction processes have been described in the art. U.S. Pat. No. 5,648,564 describes the production of xanthophylls from plant matter. Said patent discloses the extraction of zeaxanthin from Wolfberries. However, the extraction process is carried out on a fraction wherein the Brix is father high, i.e. greater than 10° Brix and thus drying is required as an intermediate stage in the process, before the extraction stage.

It has now been found that when plant matter having a Brix greater than 10 is extracted, the subsequent separation of the pulp from the extracting solvent is problematic due to generation of three phases which are difficult to separate, when the plant material before extraction is not dried. The first phase contains solids saturated with solvent, the second phase at the interface between the first and third phase contains polysaccharides, solvent and part of the lipophilic substances, e.g. carotenoids, and the third phase contains the solvent and lipophilic fraction of the plant matter. Obtaining oleoresin from the solids' phase will provide an oleoresin which contains polysaccharides and other water soluble constituents from the plant matter. This oleoresin is of poor quality, low content of the desired lipophilic substance, i.e. carotenoids and is unsuitable for use for further isolation of the carotenoid contained therein.

In view of the above, there is a long felt need for an economical, efficient process for the separation of carotenoid-containing oleoresin and carotenoids from plant matter of Brix greater than 10°.

Therefore it is an objective of the present invention to provide an economical, efficient process for the separation of carotenoid-containing oleoresin from plant matter having Brix greater than 10°.

It is a further objective of the present invention to provide a process for obtaining carotenoids in an essentially pure form from plant matter having Brix greater than 10°.

Further objectives of the invention will become apparent as the description proceeds.

SUMMARY OF THE INVENTION

The present invention provides a process for extracting carotenoids from carotenoid-containing plant matter wherein the Brix in said plant matter is greater than 10° Brix, comprising of the following steps:

i. Mixing the plant matter with water to achieve Brix not greater than 10°.

ii. Crushing the mixture from stage (i) and separating the solids from the liquid to obtain two phases, pulp and serum.

iii. Extracting the pulp to obtain carotenoid-containing plant oleoresin,

Optionally, the process may further comprise a stage of concentrating the serum to obtain a liquid concentrate of the water miscible material of the plant matter.

According to a further aspect of the present invention there is provided a process for the isolation of carotenoids from plant matter wherein the process described above further comprises a stage of isolating the carotenoid from the carotenoid-containing oleoresin obtained in stage (iii) or from the extracts of the extraction stage. Carotenes are isolated from the oleoresin thereof by diluting the oleoresin with a suitable solvent and filtering, to obtain solid carotenoid. Wherein the carotenes are isolated from the extracts, the extracts are diluted with a suitable solvent and filtered to obtain the solid carotene.

According to a further aspect of the invention when the plant oleoresin obtained, contains xanthophylls in the form of an ester or diester, the process further comprises of a stage wherein the oleoresin is subjected to saponification conditions to obtain the fatty-acid-free form of the xanthophylls.

GENERAL DESCRIPTION OF THE DRAWINGS

FIG. 1—A block diagram of the process.

Figure 2:
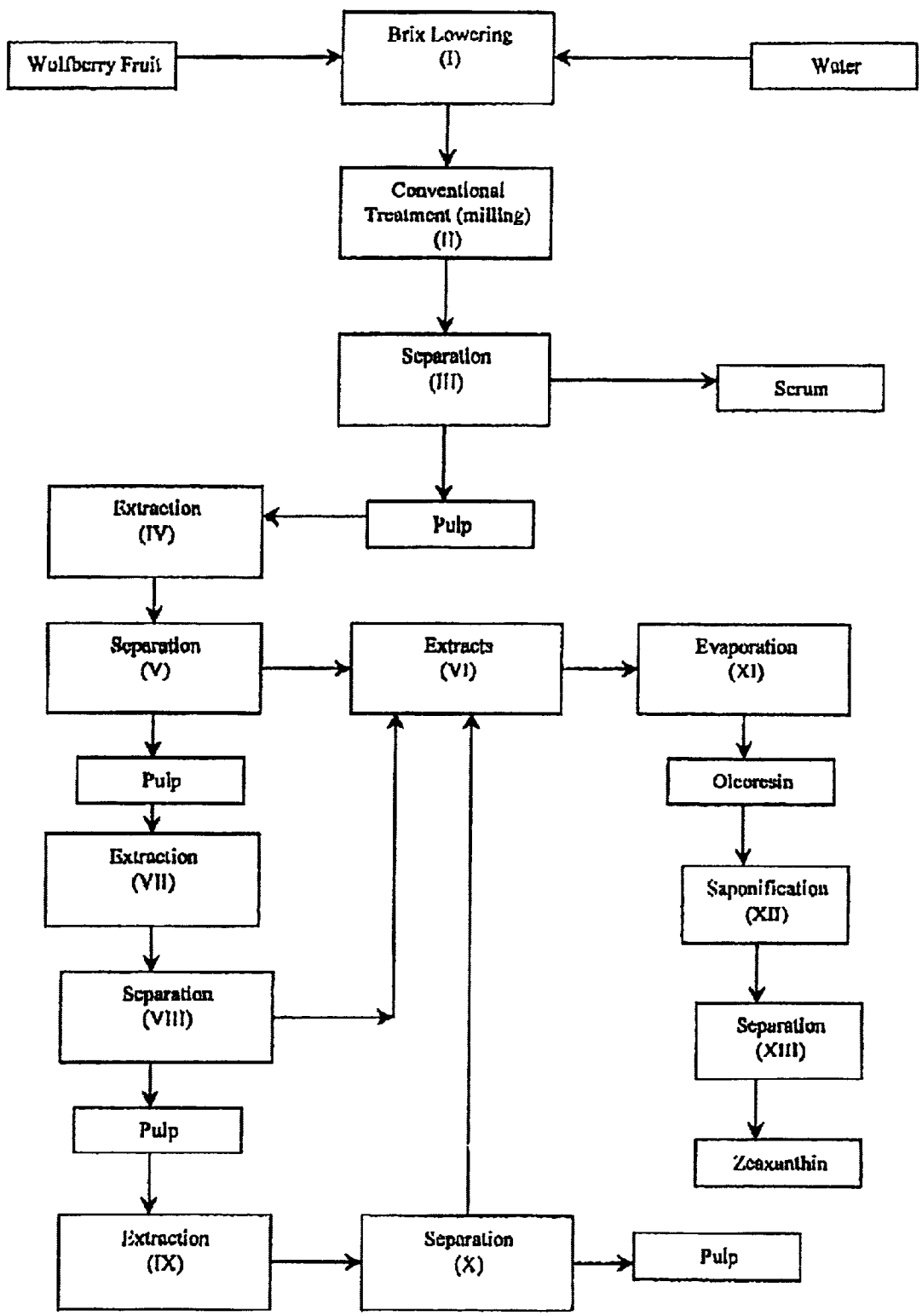

FIG. 2—A block diagram of a process for the reparation of zeaxanthin

DETAILED DESCRIPTION OF THE INVENTION

The following description is illustrative of embodiments of the invention. The following description is not to be construed as limiting, it being understood that the skilled person may carry out many obvious variations to the process.

Throughout the description, percentages and ratio of components are by weight, unless specifically noted differently. The term carotenoid encompasses carotenes and xanthophylls. Brix is defined as the measure of the total soluble solids, expressed as if they were sucrose, measured by means of a refractometer.

Carotenoid-containing plant matter suitable for the present invention are leaves, flowers, fruit and other parts of the plant. Throughout the description plant matter also includes products derived from plant matter, e.g. tomato paste, fruit, dried fruit, puree and carotenoid-containing biomass from algae. According to a particular aspect of the invention the plant matter is selected from among a group comprising of tomato paste, carrots, dried carrots Wolfberry fruit (*Lycium barbarum*), corn and Dunaliala biomass.

The carotenoids which may be extracted according to the present process include carotenes and xanthophylls. Non-limiting examples include lycopene, beta and alpha-carotene, lutein, astaxanthin, zeaxanthin, capsanthin, canthaxanthin, phytoene and phytofluene.

Throughout the description the extracting solvents referred to as suitable solvents are solvents selected based on two parameters: $\delta_H$ and $\delta_P$. A third parameter, which is $\delta_D$, has a narrow range of values and is not critical, but should preferably be as high as possible. According to the invention, $\delta_H$ should vary between 0.0 and 5.0, preferably 0.0 and 4.5 and $\delta_P$ between 0.0 and 10. If a mixture of solvents is used, the δ parameters attributed to it should be the linear combination of the δ parameters of the component solvents. While this may not be scientifically exact, it is a close enough criterion for industrial purposes. The δ parameters of all possible interesting solvents are well known. A list of them can be found, for instance, in the chapter "Solubility Parameters", of the book Handbook of Solvent Extraction, T. C. Lo, M. H. I. Baird and C. Hanson, T. Wiley Publisher (1983) pp. 25, 30 and 31, and CRC Handbook of Solubility Parameters and Other Cohesion Parameters, $2^{nd}$ Ed. (A. F. C. Barton) 1982,p.620.

It has surprisingly been found that the extraction of carotenoids from plant matter with suitable solvents selected according to certain solubility parameters, e.g. ethyl acetate, isopropanol, ethanol and acetone is facilitated when the Brix of the plant matter is below 10°. Under these conditions the extraction is more efficient and the separation of the pulp phase from the solvent phase during the process facile.

According to an embodiment of the invention, described with reference to FIG. 1, water is added to plant matter having Brix greater than 10° so as to lower the Brix of the plant matter below 10° (FIG. 1, (I)). The plant matter is mixed with the water at a temperature of about 70° C. to 100° C., preferably at a temperature of about 80° C. to 95° C. in order to facilitate the dissolution of the water miscible components e.g., polysaccharides. The plant matter is then treated by conventional operations, including crushing (FIG. 1, (II)). The treated plant matter is separated to serum and pulp (FIG. 1, (III)). The separation may be carried out by conventional means, e.g., decantation, conventional filtration or centrifugation. A majority of the water soluble components of the plant matter are contained in the serum. Said components may include anthocyanines, polyphenols and polysacoharides. The plant matter which is not soluble in water, i.e. the lipid fraction is maintained in the pulp. Hence the carotenoids are in the pulp. The pulp is then subject to extraction with a suitable solvent, preferably selected from among a group comprising of ethyl acetate, iso-propanol, ethanol and acetone or mixtures thereof (FIG. 1, IV). In order to produce good yields of oleoresin and carotenoids it is important to extract the pulp in several extraction steps. Hence, multi-stage extraction is applied to the pulp fraction. Following the extraction, the extracting solvent is separated from the extractant, i.e. the oleoresin, by conventional separation techniques as may be appreciated by the skilled artisan. A non-limiting example of a technique for separating the extracting solvent is evaporation. The oleoresin obtained contains the carotenoid. Depending on the carotenoid in the plant matter, an isolation stage may be further employed in order to obtain the carotenoid in pure form. Wherein the carotenoid is a carotene e.g. lycopene, beta and alpha-carotene the isolation of the carotenoid can be carried out by diluting the oleoresin obtained or extracts to obtain a solution of about 1% carotenoid content wherein only a small fraction of the carotenoid is dissolved, and filtering the solution to obtain solid carotenoid. The losses of carotenoid in this stage are very small and do not significantly affect the yield of the process. Wherein the carotenoid in the plant matter is in the form of an ester or diester e.g. zeaxanthin dipalmitate, the oleoresin obtained is further subjected to saponification conditions to obtain the carotenoid in free form.

According to a preferred embodiment of the invention, with reference to FIG. 2, zeaxanthin is obtained from wolfberry fruit. Thus, dry wolfberry fruit having Brix of about 80° is added to a vessel wherein water is added in order to lower the Brix below 10° (FIG. 2, I). The weight ratio between the wolfberries and the water is at least 1:8, preferably 1:10 (in this context the ratio is considered larger as the denominator of the ratio increases). Preferably, the water added is at a temperature of 70° C. to 100° C., more preferably 90° C. The hydrated wolfberries of Brix lower than 10°, preferably 5° to 7° Brix are then treated for particle size reduction, e.g. milling (FIG. 2, II). The milled hydrated wolfberries are then subject to a separation process which separates pulp from the aqueous phase. Non-limiting examples of suitable separation techniques are centrifugation and decantation (FIG. 2, III). Two phases are obtained, pulp and serum. Pulp contains lipids, carotenoids and other components which are not soluble in water. The aqueous phase obtained from decantation is also called serum and contains water soluble constituents such as polysaccharides, anthocyanines and polyphenols. Part of said water soluble constituents may be of commercial value e.g., anthocyanines and polyphenols. Thus, the serum is further processed to isolate said valuable materials. The pulp is extracted in a multi-stage extracting process, A suitable extracting solvent, preferably selected from among a group comprising of ethyl acetate, iso-propanol, ethanol and acetone or mixtures thereof is added to the pulp in the first extracting stage (FIG. 2, IV) and the pulp is extracted, preferably at a temperature in the range of about 40° C. to 65° C., more preferably about 60° C. The weight ratio between the pulp and the solvent in the extraction stages is between 1:3 to 1:6, preferably 1:4. The extract and pulp separated by conventional techniques, e.g. filtration, decantation or centrifugation (FIG. 2, V). The pulp is transferred down stream for the second extracting stage (FIG. 2, VII). The pulp and extract are again separated as described above (FIG. 2, VIII). The pulp is then extracted for the third time (FIG. 2, IX) and the extract and pulp are separated (FIG. 2, X) to obtain a spent pulp. The solvent fraction (extract) collected from the extraction stages (FIG. 2, VI) is evaporated (FIG. 2, XI) to obtain oleoresin of 10%–20% zeaxanthin fatty acid diester. The oleoresin is subjected to saponification conditions (FIG. 2, XII) in order to hydrolyze the zeaxanthin diester to obtain zeaxanthin. The saponification is carried out at a temperature of about 70° C. to 80° C. in a mixture containing an aqueous solution of KOH, ethanol and hexane for about 1 hour. Upon hydrolysis of the zeaxanthin diester-containing oleoresin, zeaxanthin crystals precipitate and the mixture is filtered (FIG. 2, XIII). The solid fraction obtained contains about 70% to 90% zeaxanthin.

According to yet a further embodiment of the invention, the solvent from the first extracting stage is recycled to the first extracting stage as to further enrich the solvent with higher concentrations of solvent. This has economical advantages and improves the efficiency of the process. The extraction conditions and techniques appropriate for the process can easily be understood and determined by the skilled artisan.

According to a further embodiment of the present invention, oleoresin containing about 5%–6% lycopene is obtained from tomato concentrate having 30° Brix. The tomato concentrate is hydrated with water to obtain a hydrated tomato concentrate of having Brix lower than 10°, preferably about 5°. The weight ratio between the tomato concentrate and water is at least 1:3, preferably 1:6. The hydrated tomato concentrate is mixed and allowed to settle. Then the hydrated tomato concentrate is centrifuged to separate the solid phase (pulp) from the liquid aqueous phase (serum). The pulp having Brix less than 10°, preferably about 5°, is extracted with a suitable solvent, preferably selected from among a group comprising of ethyl acetate, iso-propanol, ethanol and acetone or mixtures thereof, preferably at a temperature in the, range of about 40° C. to 65° C., more preferably about 60° C. Preferably the extraction is carried out in a number of extraction stages. Said number may be two or greater. When a multi-stage extraction is carried out the extracts are combined before subsequent concentration. In order to maintain an extraction process which is economical it is advantageous to maintain a ratio between the pulp and the solvent of 1:3 to 1:6, preferably 1:4. The extract from the extraction stage is concentrated to obtain a tomato oleoresin with a lycopene concentration of about 5% to 6%. Concentration of the extract may by be carried out by methods known in the art e.g., evaporation of the solvent. According to a further embodiment of the invention, substantially pure lycopene may be obtained from the tomato oleoresin or extracts by adding to the tomato oleoresin or extracts solvent, preferably ethyl acetate to obtain a mixture containing 1% lycopene and then filtering the mixture to obtain solid lycopene.

In yet a further preferred embodiment of the present invention a carrot oleoresin containing β-carotene and α-carotene are obtained from carrots which have Brix of about 12°. Optionally, the oleoresin may be produced from dry carrots which have Brix of about 30° to 40°. Carrot pieces are hydrated with a sufficient amount of water which lowers the Brix of the mixture below 10°, preferably about 5° to 7°. Wherein fresh carrots are hydrated, the weight ratio between the carrots and water is at least 1:1. Wherein dry carrots are hydrated, the weight ratio between the dry carrots and water is at least 1:3, preferably 1:6. Preferably, hydration is carried out with water having a temperature in the range of 70° C. to 100° C., more preferably 90° C. The hydrated carrots are separated to a solid phase (pulp) and liquid aqueous phase (serum). Preferably, separation is effected via centrifugation. The resultant pulp has Brix lower than 10°, preferably about 5° to 7°. The pulp having Brix less than 10°, preferably about 5° to 7°, is extracted with a suitable solvent, preferably selected from among a group comprising of ethyl acetate, iso-propanol, ethanol and acetone or mixtures thereof, preferably at a temperature in the range of about 40° C. to 65° C., more preferably about 60° C. Preferably the extraction is carried out in a number of extraction stages. Said number may be two or greater. When a multi-stage extraction is carried out the extracts are combined before subsequent concentration. In order to maintain an extraction process which is economical, it is advantageous to maintain a ratio between the pulp and the solvent of 1:2 to 1:4, preferably 1:2.5. The extract from the extraction stage is concentrated to obtain a carrot olcoresin with β-carotene and α-carotene concentration of about 5% to 6% wherein the ratio between the two carotenes correlates with the ratio in the plant matter. Concentration of the extract may by be carried out by methods known in the art e.g., evaporation of the solvent. According to a further embodiment of the invention said carotenes may be isolated from the plant matter to obtain 60–80% pure alpha and beta carotenes by adding solvent to the oleoresin or extracts, preferably ethyl acetate to obtain a mixture containing about 1% carotenes and then filtering the mixture to obtain solid carotenes.

The extraction stage carried out in the present invention may be carried out under various conditions, as may be appreciated by the skilled artisan, depending on the technology available and the product desired. Accordingly, the parameters of the extraction stage, i.e. number of extraction stages, temperature, amount of solvent employed, recycling and makeup streams of solvent and balances based on evaporation and water-solvent separation loses can be modified and adjusted to meet specific requirement.

The extraction stage of the present invention may be carried out according to techniques known in the art e.g., continuous and batch type extraction.

The present invention is advantageous in that it provides an efficient and economical process which facilitates the separation of carotenoids and plant oleoresin from plant matter which has Brix greater than 10°, wherein said process is carried out with solvents which are considered to be safe according to standards employed in the food industry.

EXAMPLES

Example 1

Lycopene Containing Tomato Oleoresin from Tomato Paste of 30°Bx 100 g of Tomato Paste were mixed with 600 g water. Mixture was centrifuged 3 min at 3000 Rpm. Settling with 5°Bx and moisture less that 82% was extracted 3 times with 250 g ethyl acetate at a temperature of 60° C. The extracts were combined and evaporated under reduced pressure to apparent dryness to form an organic solvent-free homogenous oleoresin. Lycopene concentration in oleoresin 5–6%.

Example 2

Comparative Example

The following Example demonstartes the results of a process for obtaining lycopene containing Tomato oleoresin from tomato paste without adjusting the Brix. 100 g of Tomato Paste were extracted 3 time with 250 g ethyl acetate at a temperature of 60° C. The extracts were combined and evaporated under reduced pressure to apparent dryness to form an organic solvent-free oleoresin. Product oleoresin was non-homogenous, with caramel granules. Yield of extraction less that 50%. Lycopene concentration in oleoresin 1.5–2%.

Example 3

Zeaxanthin Containing Oleoresin from Wolfberries (*Lycium barbarum*)

100 g of berries were hydrated and milled with 1000 g hot water (80–100° C.). Paste was centrifuged 3 min at 3000 Rpm. Settling with 5–71 Bx and moisture less that 82% was extracted 3 times with 400 g ethyl acetate at a temperature of 60° C. The extracts were combined, filtered and evaporated under reduced pressure to apparent dryness to form an organic solvent-free homogenous oleoresin containing zeaxanthin dipalmitate for saponification. Zeaxanthin dipalmitate concentration in oleoresin 13–15%.

Example 4

β-Carotene and α-Carotene Containing Oleoresin from Dry Carrots 100 g of dry carrot particles were hydrated and milled with 700 g hot water (80–100° C.). Paste was centrifuged 3 min at 3000 rpm. Settling with 5–70 Brix and moisture less that 82% was extracted 3 times with 300 g ethyl acetate and temperature 60° C. The extracts were combined, filtered and evaporated under reduced pressure to apparent dryness to form an organic solvent-free homogenous oleoresin. β-carotene and α-carotene concentration in oleoresin 5–6%.

While embodiments of the invention have been described by way of description, it will be apparent that the invention may be carried out with many modifications, variations and adaptations, without departing from its spirit or exceeding the scope of the claims.

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed is:

1. A process for extracting carotenoids from carotenoid-containing plant matter wherein the Brix in said plant matter is greater than 10° Brix, comprising of the following steps:
   i. Mixing the plant matter with water to achieve Brix not greater than 10°;
   ii. Crushing the mixture from stage (i) and separating the solids from the liquid to obtain two phases, pulp and serum.
   iii. Extracting the pulp to obtain carotenoid-containing plant oleoresin.

2. A process according to claim 1 wherein the carotenoids are carotenes or xanthophylls.

3. A process according to claim 2 where in the carotenoids are selected from among a group comprising of lycopene, beta and alpha-carotene, lutein, astaxanthin, zeaxanthin, capsanthin, canthaxanthin, phytoene and phytofluene.

4. A process according to claim 1 wherein the plant matter is selected from among a group comprising of tomato paste, carrots and dried carrots.

5. A process according to claim 4 further comprising a stage of isolating the carotenoid from the oleoresin or extracting solvent.

6. A process according to claim 5 for obtaining lycopene, alpha-carotene and beta-carotene.

7. A process according to claim 1 wherein the plant matter is selected from among a group comprising of Wolfberry fruit (*Lycium barbarum*), corn and Dunaliala biomass.

8. A process according to claim 7 further comprising a stage of isolating a carotenoid xanthophyll.

9. A process according to claim 8 wherein the xanthophyll is obtained via saponification of the xanthophyll ester obtained in the oleoresin.

10. A process according to claim 1 wherein stage (i) is carried out in water at a temperature of about 70° C. to 100° C.

11. A process according to claim 1 wherein the extracting stage is carried out in a solvent or mixture thereof having $\delta_H$ between 0.0 and 5.0 and $\delta_P$ between 0.0 and 10.

12. A process according to claim 11 wherein the solvent employed is selected from among a group comprising of ethyl acetate, iso-propanol, ethanol and acetone or mixtures thereof.

13. A process according to claim 1 wherein the extraction is carried out in several stages.

14. A process according to claim 1 comprising a further stage of concentrating the serum to obtain a liquid concentrate of the water miscible material of the plant matter.

* * * * *